United States Patent
Yamamoto et al.

(10) Patent No.: US 6,787,557 B2
(45) Date of Patent: Sep. 7, 2004

(54) RICE BLAST CONTROL AGENTS

(75) Inventors: Kazumi Yamamoto, Yokohama (JP);
Takeshi Teraoka, Yokohama (JP);
Hiroshi Kurihara, Yokohama (JP);
Makoto Matsumura, Yokohama (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 10/276,865

(22) PCT Filed: May 29, 2001

(86) PCT No.: PCT/JP01/04501
§ 371 (c)(1),
(2), (4) Date: Nov. 20, 2002

(87) PCT Pub. No.: WO01/92231
PCT Pub. Date: Dec. 6, 2001

(65) Prior Publication Data
US 2003/0176459 A1 Sep. 18, 2003

(30) Foreign Application Priority Data
May 30, 2000 (JP) .................................. 2000-160316

(51) Int. Cl.[7] ................... A01N 43/42; C07D 215/233
(52) U.S. Cl. ................................. 514/312; 546/153
(58) Field of Search ........................ 514/312; 546/153

(56) References Cited

FOREIGN PATENT DOCUMENTS

| | | | |
|---|---|---|---|
| EP | 990648 | * | 4/2000 |
| WO | 98/55460 | | 12/1998 |

* cited by examiner

*Primary Examiner*—Patricia L. Morris
(74) *Attorney, Agent, or Firm*—Wenderoth, Lind & Ponack, L.L.P.

(57) ABSTRACT

Disclosed is a compound of formula (1) or an acid addition salt thereof which has excellent rice blast control effect:

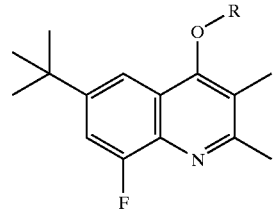

(1)

wherein
R represents a hydrogen atom, —COR$^1$, —COOR$^1$, in which R$^1$ represents alkyl having 1 to 4 carbon atoms, —COCH$_2$OCH$_3$, or —COCH$_2$OCOCH$_3$.

14 Claims, No Drawings

RICE BLAST CONTROL AGENTS

BACKGROUND OF THE INVENTION

1. Field of the Invention

The present invention relates to a controlling agent for rice blast.

2. Background Art

Up to now, a large number of active compounds having control effect against various plant diseases have been found, and various controlling agents for plant diseases, comprising them as active ingredients have been developed. For example, from the viewpoint of appearance of resistant strains, however, there is room for improvement in control effect of the controlling agents.

Blast may be mentioned as one of plant diseases, and is induced by infection of fungi of the genus Pyricularia which are a kind of mold fungi and belong to deuteromycotina. In particular, an outbreak of rice blast sometimes takes place in abnormal weather such as low temperature or much rain in the summer period, and, thus, rice blast is one of the most serious diseases of rice.

For this reason, the development of controlling agents having excellent control effect against rice blast has been desired.

International Publication WO 98/55460 discloses 4-quinolinol derivatives and fungicides for agricultural and horticultural applications, comprising these derivatives as active ingredients. In this publication, however, there is no description on usefulness of 2,3-dimethyl-6-t-butyl-8-fluoro-4-quinolinol derivatives.

SUMMARY OF THE INVENTION

The present inventors have now found that, among 4-quinolinol derivatives, those having t-butyl (tertiary butyl) at the 6-position and fluorine at the 8-position, that is, 2,3-dimethyl-6-t-butyl-8-fluoro-4-quinolinol derivatives, have significantly high control effect against rice blast. This control effect is significantly superior to that attained by other 4-quinolinol derivatives disclosed, for example, in International Publication WO 98/55460. The present invention has been made based on such finding.

Accordingly, it is an object of the present invention to provide a compound and a controlling agent which have excellent control effect against rice blast.

According to one aspect of the present invention, there is provided a compound of formula (1) or an acid addition salt thereof:

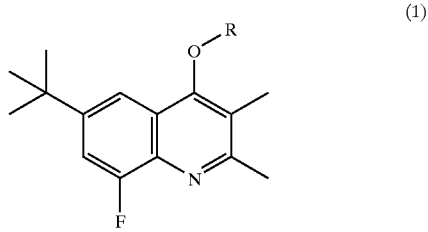

(1)

wherein

R represents a hydrogen atom, —COR$^1$, —COOR$^1$, in which R$^1$ represents alkyl having 1 to 4 carbon atoms, —COCH$_2$OCH$_3$, or —COCH$_2$OCOCH$_3$.

According to another aspect of the present invention, there is provided a controlling agent for rice blast, comprising as active ingredients at least one compound selected from the group consisting of the compounds of formula (1) or acid addition salts thereof.

DETAILED DESCRIPTION OF THE INVENTION

Compounds of Formula (1)

The present invention relates to the compounds of formula (1) (2,3-dimethyl-6-t-butyl-8-fluoro-4-quinolinol derivatives) or acid addition salts thereof. The compounds of formula (1) or acid addition salts thereof have excellent control effect against rice blast (*Pyricularia oryzae*) and can be advantageously used as controlling agents for rice blast.

In the compounds of formula (1), R represents a hydrogen atom, —COR$^1$, —COOR$^1$, —COCH$_2$OCH$_3$, or —COCH$_2$OCOCH$_3$, wherein R$^1$ represents alkyl having 1 to 4 carbon atoms, for example, methyl, ethyl, propyl, or butyl.

In formula (1), when R represents a hydrogen atom, the compounds of formula (1) may take a structure of formula (2) which is a tautomer of the compounds of formula (1). It would be apparent to a person having ordinary skill in the art that the compounds of formula (1) embrace the compounds of formula (2).

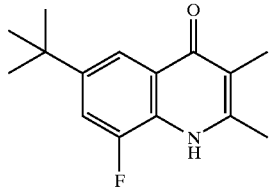

(2)

In the present invention, the term "acid addition salt" refers to salts, which are generally usable in the fields of agriculture and horticulture, for example, hydrochlorides, nitrates, sulfates, phosphates, and acetates.

It should be noted that the compounds of formula (1) may take the form of hydrates or solvates. In the present invention, such hydrates and solvates are also embraced in the compounds of formula (1).

Specific examples of compounds of formula (1) include:

2,3-dimethyl-6-t-butyl-8-fluoro-4-hydroxyquinoline;
2,3-dimethyl-6-t-butyl-8-fluoro-4-acetylquinoline;
2,3-dimethyl-6-t-butyl-8-fluoro-4-propionyl-quinoline;
2,3-dimethyl-6-t-butyl-8-fluoro-4-butyrylquinoline;
2,3-dimethyl-6-t-butyl-8-fluoro-4-valerylquinoline;
2,3-dimethyl-6-t-butyl-8-fluoro-4-methoxycarbonyl-quinoline;
2,3-dimethyl-6-t-butyl-8-fluoro-4-ethoxycarbonyl-quinoline;
2,3-dimethyl-6-t-butyl-8-fluoro-4-n-propoxy-carbonylquinoline;
2,3-dimethyl-6-t-butyl-8-fluoro-4-n-butoxycarbonyl-quinoline;
2,3-dimethyl-6-t-butyl-8-fluoro-4-methoxyacetyl-quinoline; and
2,3-dimethyl-6-t-butyl-8-fluoro-4-acetoxyacetyl-quinoline.

Production Process of Compounds of Formula (1)

The compounds of formula (1) according to the present invention may be synthesized by any appropriate process regarding the formation of a bond or the introduction of a substituent.

For example, a compound of formula (1) can be produced from 4-t-butyl-2-fluoroaniline, which can be synthesized by a conventional method, according to the following scheme.

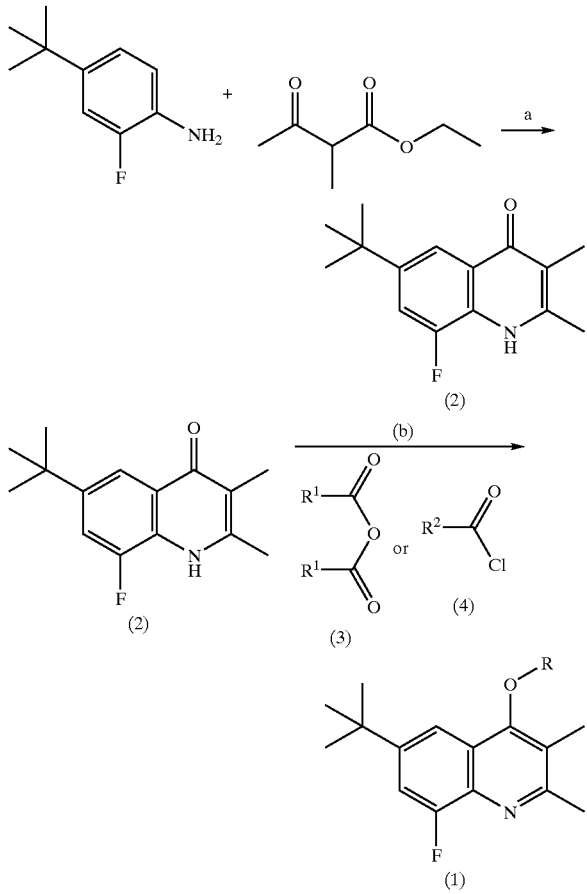

wherein
R represents a hydrogen atom, —COR¹, —COOR¹, in which R¹ represents alkyl having 1 to 4 carbon atoms, —COCH₂OCH₃, or —COCH₂OCOCH₃, and R² represents R¹, —OR¹, —CH₂OCH₃, or —CH₂OCOCH₃.

According to this scheme, a compound of formula (2) is first provided (step (a)), and the compound of formula (2) is then reacted with the compound of formula (3) or (4) in the presence or absence of a base (step (b)) to give the compound of formula (1).

The above scheme will be described in more detail.

Step (a)

At the outset, a compound of formula (2) is prepared from 4-t-butyl-2-fluoroaniline and ethyl 2-methyl-acetoacetate, for example, according to J. Am. Chem. Soc. 70, 2402 (1948), Tetrahedron Lett. 27, 5323 (1986). The compound of formula (2) corresponds to the compound of formula (1) wherein R represents a hydrogen atom. 4-t-Butyl-2-fluoroaniline used herein may be prepared by a conventional method described, for example, in Chem. Abs. 42, 2239 or J. Chem. Soc., Chem. Commun., 1992, 595.

Step (b)

Next, when a compound of formula (1), wherein R represents a group other than a hydrogen atom, is desired, this compound can be produced by reacting the compound of formula (2) with the compound of formula (3) or (4) in the presence or absence of a base.

Bases usable herein include, for example, organic amines, such as triethylamine and pyridine, and inorganic bases, such as sodium carbonate, potassium carbonate, and sodium hydride. The compound of formula (3) or (4) is preferably used in an amount of 1 to 50 equivalents, more preferably 1 to 10 equivalents, based on the compound of formula (2). The reaction in step (b) may be carried out in the absence of a solvent or in the presence of an organic solvent inert to the reaction, for example, dimethylformamide or tetrahydrofuran, for example, in the temperature range of 0 to 140° C.

Controlling Agent for Rice Blast

The controlling agent for rice blast according to the present invention comprises as an active ingredient at least one compound selected from the group consisting of the compounds of formula (1) or acid addition salts thereof.

The expression "comprising as an active ingredient" as used herein means that a carrier according to the formulation may of course be incorporated and, in addition, other chemical agents usable in combination with the compound of the present invention may be incorporated.

Accordingly, when the compound of formula (1) is used as a controlling agent for rice blast, the compound of formula (1) as such may be used. In general, however, the compound of formula (1) may be mixed, for example, with suitable solid carriers, liquid carriers, gaseous carriers, surfactants, dispersants and/or other adjuvants for formulations, to prepare any suitable formulation, such as emulsifiable concentrates, liquid formulations, wettable powder, dust formulation, granules, oil solutions, aerosols, or flowables.

Solid carriers usable herein include, for example, talc, bentonite, clay, kaolin, diatomaceous earth, vermiculite, white carbon, and calcium carbonate.

Examples of liquid carriers include: alcohols, such as methanol, n-hexanol, and ethylene glycol; ketones, such as acetone, methyl ethyl ketone, and cyclohexanone; aliphatic hydrocarbons, such as n-hexane, kerosine, and kerosene; aromatic hydrocarbons, such as toluene, xylene, and methylnaphthalene; ethers, such as diethyl ether, dioxane, and tetrahydrofuran; esters, such as ethyl acetate; nitriles, such as acetonitrile and isobutyronitrile; acid amides, such as dimethylformamide and dimethylacetamide; vegetable oils, such as soy bean oil and cotton seed oil; dimethylsulfoxide; and water.

Gaseous carriers include, for example, LPG, air, nitrogen, carbon dioxide, and dimethyl ether.

Surfactants or dispersants usable, for example, for emulsifying, dispersing, or wetting the compound of formula (1) include, for example, alkylsulfonic esters, alkylsulfonic acid salts, alkylarylsulfonic acid salts, polyoxyalkylene alkyl ethers, polyoxyalkylene alkylaryl ethers, polyhydric alcohol esters, and lignin sulfonic acid salts.

Adjuvants usable for improving the properties of formulations include, for example, carboxymethylcellulose, gum arabic, polyethylene glycol, and calcium stearate.

At least two members may be selected from the above group of carriers, group of surfactants, group of dispersants, and group of adjuvants (the selected members may belong to the same group or different groups) and used in combination.

The content of the compound of formula (1) or acid addition salt thereof in the controlling agent for rice blast may be properly varied by taking into consideration formulations, application methods and application environment of the controlling agent and other conditions. The content of the compound of formula (1) is generally 1 to 75% by weight, preferably 5 to 30% by weight, when the controlling agent is an emulsifiable concentrate; generally 0.3 to 25% by weight, preferably 1 to 3% by weight, when the controlling agent is dust; generally 1 to 90% by weight, preferably 5 to 50% by weight, when the controlling agent is wettable powder; and generally 0.5 to 50% by weight, preferably 2 to 30% by weight, when the controlling agent is granules.

The controlling agent for rice blast according to the present invention is generally used as such or after dilution.

Methods of application of the controlling agent for rice blast according to the present invention include, for example, application to rice plant per se (application to stems and leaves), application to nursery boxes, application to soil (admixing with soil or side dressing(i.e. what is called "sokujou" in Japanese), application to field water (application to water surface or application to regular paddy field), and application to seeds (seed treatment).

According to a further aspect of the present invention, there is provided a method for controlling rice blast, comprising the step of applying the compound of formula (1) or acid addition salt thereof to a rice plant per se, soil, or field water.

The controlling agent for rice blast according to the present invention may be applied in an amount which is properly determined by taking into consideration, for example, application environment and state of growth and development of rice plant. For example, however, when the controlling agent is applied to soil or field water for the growth and development of rice plants, the amount of the controlling agent in terms of the amount of the active ingredient is preferably 9 to 500 g, more preferably 30 to 300 g, per 10 ares.

Further, the controlling agent for rice blast according to the present invention may be used as a mixture, for example, with other fungicides, bactericides, insecticides, miticides, herbicides, plant growth-regulating agents, or fertilizers.

EXAMPLES

The following examples further illustrate the present invention, but are not intended to limit it.

Production Examples

Compounds 1 to 11 according to the present invention were produced as follows. For comparison, compounds 12 to 14 were produced in the same manner as used in the production of the compounds 1 to 11.

Production of 4-t-butyl-2-fluoroaniline

SELECTFLUOR (manufactured by Aldrich Chemical Company Inc.) (1-chloromethyl-4-fluoro-1,4-diazoniabicyclo [2,2,2]octanebistetrafluoroborate) (15 g) was added to acetonitrile (200 ml), and mixture was heated at 70° C. for 30 min to dissolve SELECTFLUOR in acetonitrile. The reaction solution thus obtained was cooled to 60° C., and 4-t-butyl-acetanilide (5.7 g) was added to the cooled reaction solution. The mixture was stirred at 100° C. for one hr, and the reaction solution was then allowed to stand for cooling. The cooled reaction solution was then added to water (200 ml), followed by extraction with ethyl acetate (100 ml, twice). The ethyl acetate layer was washed with saturated brine and was dried over anhydrous sodium sulfate, and the solvent was then removed under the reduced pressure. The crude product thus obtained was purified by chromatography on silica gel (Wako Gel C-200 manufactured by Wako Pure Chemical Industries, Ltd., elution solvent: n-hexane-ethyl acetate (10:1)) to give 4-t-butyl-2-fluoro-acetanilide (3.06 g). This 4-t-butyl-2-fluoro-acetanilide (3.67 g) was added to a mixed solution composed of ethanol (30 ml) and concentrated hydrochloric acid (15 ml), and the mixture was stirred at 95° C. for 2 hr. The reaction solution was allowed to stand for cooling, and the cooled reaction solution was then poured into water, followed by neutralization with a saturated aqueous sodium hydrogencarbonate solution and extraction with ethyl acetate. The ethyl acetate layer was washed with a saturated aqueous sodium hydrogencarbonate solution and saturated brine, and was dried over anhydrous sodium sulfate. The solvent was then removed under the reduced pressure to give 4-t-butyl-2-fluoroaniline (3.49 g). $^1$H-NMR data on this compound in deutro-chloroform were as shown below.

δ (ppm): 7.01 (1H, dd), 6.95 (1H, dd), 6.73 (1H, m), 1.28 (9H,s)

Compound 1: 2,3-Dimethyl-6-t-butyl-8-fluoro-4-hydroxyquinoline 4-t-Butyl-2-fluoroaniline (4.79 g) prepared according to the above process and ethyl 2-methyl-acetoacetate (4.96 g) were refluxed in toluene (60 ml) in the presence of trifluoroboron etherate (0.3 ml) for 3 hr to obtain a reaction solution. The reaction solution thus obtained was washed with a saturated aqueous sodium hydrogencarbonate solution and saturated brine and was dried over anhydrous sodium sulfate. The solvent was then removed under the reduced pressure. The reaction product was refluxed in diphenyl ether (80 ml) for one hr and was allowed to stand for cooling. The precipitated product was then collected by filtration under the reduced pressure to give 2,3-dimethyl-6-t-butyl-8-fluoro-4-hydroxyquinoline (compound 1, 1.66 g). $^1$H-NMR data on this compound in deutro-DMSO (dimethyl sulfoxide) were as shown below.

δ (ppm): 11.27 (1H, br.s), 7.83 (1H, s), 7.59 (1H, br.d), 2.41 (3H, s), 1.96 (3H, s), 1.31 (9H, s)

Compound 2: 2,3-Dimethyl-6-t-butyl-8-fluoro-4-acetylquinoline

The compound 1 (50 mg) was stirred in acetic anhydride (3 ml) at 120° C. for 3 hr to obtain a reaction solution. Acetic anhydride was removed from the reaction solution under the reduced pressure. The residue was dissolved in ethyl acetate. The solution was washed with a saturated aqueous sodium hydrogencarbonate solution and saturated brine and was then dried over anhydrous sodium sulfate, and the solvent was then removed under the reduced pressure. The crude product was purified by chromatography on silica gel (Wako Gel C-200, elution solvent: n-hexane-ethyl acetate (5:1)) to give 2,3-dimethyl-6-t-butyl-8-fluoro-4-acetylquinoline (compound 2, 35.7 mg). $^1$H-NMR data on this compound in deutro-chloroform were as shown below.

δ (ppm): 7.43 (1H, dd), 7.37 (1H, d), 2.78 (3H, s), 2.51 (3H, s), 2.26 (3H, s), 1.38 (9H, s)

Compound 3: 2,3-Dimethyl-6-t-butyl-8-fluoro-4-propionylquinoline

In tetrahydrofuran (3 ml) was suspended 60% sodium hydride (20 mg). The compound 1 (124 mg) was added to the suspension under ice cooling, and the mixture was stirred for 30 min. Further, propionyl chloride (200 μl) was added thereto, and the mixture was stirred for 3 hr. The reaction solution thus obtained was poured into ice water, and the mixture was extracted with ethyl acetate. The ethyl acetate layer was washed with a saturated aqueous sodium hydrogencarbonate solution and saturated brine and was then dried over anhydrous sodium sulfate. The solvent was then removed under the reduced pressure. The crude product was purified by chromatography on silica gel (Wako Gel C-200, elution solvent: n-hexane-ethyl acetate (3:1)) to give 2,3-dimethyl-6-t-butyl-8-fluoro-4-propionylquinoline (compound 3, 21 mg). $^1$H-NMR data on this compound in deutro-chloroform were as shown below.

δ (ppm): 7.42 (1H, dd), 7.36 (1H, d), 2.81 (2H, q), 2.75 (3H, s), 2.25 (3H, s), 1.43 (3H, t), 1.37 (9H, s)

Compound 4: 2,3-Dimethyl-6-t-butyl-8-fluoro-4-butyrylquinoline

In tetrahydrofuran (3 ml) was suspended 60% sodium hydride (20 mg). The compound 1 (124 mg) was added to the suspension under ice cooling, and the mixture was stirred for 30 min. Further, butyryl chloride (200 µl) was added thereto, and the mixture was stirred for 3 hr. The reaction solution thus obtained was poured into ice water, and the mixture was extracted with ethyl acetate. The ethyl acetate layer was washed with a saturated aqueous sodium hydrogencarbonate solution and saturated brine and was then dried over anhydrous sodium sulfate. The solvent was then removed under the reduced pressure. The crude product was purified by chromatography on silica gel (Wako Gel C-200, elution solvent: n-hexane-ethyl acetate (3:1)) to give 2,3-dimethyl-6-t-butyl-8-fluoro-4-butyrylquinoline (compound 4, 64 mg). $^1$H-NMR data on this compound in deutro-chloroform were as shown below.

δ (ppm): 7.43 (1H, dd), 7.37 (1H, d), 2.76 (2H, t), 2.75 (3H, s), 2.25 (3H, s), 1.94 (2H, m), 1.37 (9H, s), 1.15 (3H, t)

Compound 5: 2,3-Dimethyl-6-t-butyl-8-fluoro-4-valerylquinoline

In tetrahydrofuran (3 ml) was suspended 60% sodium hydride (20 mg). The compound 1 (124 mg) was added to the suspension under ice cooling, and the mixture was stirred for 30 min. Further, valeryl chloride (200 µl) was added thereto, and the mixture was stirred for 3 hr. The reaction solution thus obtained was poured into ice water, and the mixture was extracted with ethyl acetate. The ethyl acetate layer was washed with a saturated aqueous sodium hydrogencarbonate solution and saturated brine and was then dried over anhydrous sodium sulfate. The solvent was then removed under the reduced pressure. The crude product was purified by chromatography on silica gel (Wako Gel C-200, elution solvent: n-hexane-ethyl acetate (3:1)) to give 2,3-dimethyl-6-t-butyl-8-fluoro-4-valerylquinoline (compound 5, 120 mg). $^1$H-NMR data on this compound in deutro-chloroform were as shown below.

δ (ppm): 7.42 (1H, dd), 7.37 (1H, d), 2.78 (2H, t), 2.75 (3H, s), 2.25 (3H, s), 1.89 (2H, m), 1.56 (2H, m), 1.37 (9H, s), 1.03 (3H, t)

Compound 6: 2,3-Dimethyl-6-t-butyl-8-fluoro-4-methoxycarbonylquinoline

In tetrahydrofuran (3 ml) was suspended 60% sodium hydride (20 mg). The compound 1 (124 mg) was added to the suspension under ice cooling, and the mixture was stirred for 30 min. Further, methyl chloroformate (200 µl) was added thereto, and the mixture was stirred for 3 hr. The reaction solution thus obtained was poured into ice water, and the mixture was extracted with ethyl acetate. The ethyl acetate layer was washed with a saturated aqueous sodium hydrogencarbonate solution and saturated brine and was then dried over anhydrous sodium sulfate. The solvent was then removed under the reduced pressure. The crude product was purified by chromatography on silica gel (Wako Gel C-200, elution solvent: n-hexane-ethyl acetate (3:1)) to give 2,3-dimethyl-6-t-butyl-8-fluoro-4-methoxycarbonyl-quinoline (compound 6, 100 mg). $^1$H-NMR data on this compound in deutro-chloroform were as shown below.

δ (ppm): 7.45 (1H, br.s), 7.43 (1H, dd), 4.00 (3H, s), 2.76 (3H, s), 2.31 (3H, s), 1.38 (9H, s)

Compound 7: 2,3-Dimethyl-6-t-butyl-8-fluoro-4-ethoxycarbonylquinoline

In tetrahydrofuran (10 ml) was suspended 60% sodium hydride (60 mg). The compound 1 (200 mg) was added to the suspension under ice cooling, and the mixture was stirred for 30 min. Further, ethyl chloroformate (200 µl) was added thereto, and the mixture was stirred for 3 hr. The reaction solution thus obtained was poured into ice water, and the mixture was extracted with ethyl acetate. The ethyl acetate layer was washed with a saturated aqueous sodium hydrogencarbonate solution and saturated brine and was then dried over anhydrous sodium sulfate. The solvent was then removed under the reduced pressure. The crude product was purified by chromatography on silica gel (Wako Gel C-200, elution solvent: n-hexane-ethyl acetate (3:1)) to give 2,3-dimethyl-6-t-butyl-8-fluoro-4-ethoxycarbonyl-quinoline (compound 7, 220 mg). $^1$H-NMR data on this compound in deutro-chloroform were as shown below.

δ (ppm): 7.45 (1H, br.s), 7.43 (1H, dd), 4.40 (2H, q), 2.32 (3H, s), 2.04 (3H, s), 1.44 (3H, t), 1.38 (9H, s)

Compound 8: 2,3-Dimethyl-6-t-butyl-8-fluoro-4-n-propoxy-carbonylquinoline

In tetrahydrofuran (3 ml) was suspended 60% sodium hydride (20 mg). The compound 1 (124 mg) was added to the suspension under ice cooling, and the mixture was stirred for 30 min. Further, n-propyl chloroformate (200 µl) was added thereto, and the mixture was stirred for 3 hr. The reaction solution thus obtained was poured into ice water, and the mixture was extracted with ethyl acetate. The ethyl acetate layer was washed with a saturated aqueous sodium hydrogencarbonate solution and saturated brine and was then dried over anhydrous sodium sulfate. The solvent was then removed under the reduced pressure. The crude product was purified by chromatography on silica gel (Wako Gel C-200, elution solvent: n-hexane-ethyl acetate (3:1)) to give 2,3-dimethyl-6-t-butyl-8-fluoro-4-n-propoxycarbonyl-quinoline (compound 8, 96 mg). $^1$H-NMR data on this compound in deutro-chloroform were as shown below.

δ (ppm): 7.45 (1H, br.s), 7.43 (1H, dd), 4.35 (2H, t), 2.75 (3H, s), 2.31 (3H, s), 1.82 (2H, m), 1.38 (9H, s), 1.04 (3H, t)

Compound 9: 2,3-Dimethyl-6-t-butyl-8-fluoro-4-n-butoxy-carbonylquinoline

In tetrahydrofuran (10 ml) was suspended 60% sodium hydride (60 mg). The compound 1 (200 mg) was added to the suspension under ice cooling, and the mixture was stirred for 30 min. Further, n-butyl chloroformate (200 µl) was added thereto, and the mixture was stirred for 3 hr. The reaction solution thus obtained was poured into ice water, and the mixture was extracted with ethyl acetate. The ethyl acetate layer was washed with a saturated aqueous sodium hydrogencarbonate solution and saturated brine and was then dried over anhydrous sodium sulfate. The solvent was then removed under the reduced pressure. The crude product was purified by chromatography on silica gel (Wako Gel C-200, elution solvent: n-hexane-ethyl acetate (3:1)) to give 2,3-dimethyl-6-t-butyl-8-fluoro-4-n-butoxycarbonyl-quinoline (compound 9, 142 mg). $^1$H-NMR data on this compound in deutro-chloroform were as shown below.

δ (ppm): 7.45 (1H, d), 7.43 (1H, dd), 4.35 (2H, t), 2.75 (3H, s), 2.32 (3H, s), 1.77 (2H, m), 1.48 (2H, m), 1.38 (9H, s), 0.99 (3H, t)

Compound 10: 2,3-Dimethyl-6-t-butyl-8-fluoro-4-methoxyacetylquinoline

In tetrahydrofuran (10 ml) was suspended 60% sodium hydride (165 mg). The compound 1 (680 mg) was added to the suspension under ice cooling, and the mixture was stirred for 30 min. Further, methoxyacetyl chloride (200 µl) was added thereto, and the mixture was stirred for 3 hr. The reaction solution thus obtained was poured into ice water, and the mixture was extracted with ethyl acetate. The ethyl acetate layer was washed with a saturated aqueous sodium hydrogencarbonate solution and saturated brine and was then dried over anhydrous sodium sulfate. The solvent was then removed under the reduced pressure. The crude product was purified by chromatography on silica gel (Wako Gel C-200, elution solvent: n-hexane-ethyl acetate (3:1)) to give 2,3-dimethyl-6-t-butyl-8-fluoro-4-methoxyacetylquinoline (compound 10, 390 mg). $^1$H-NMR data on this compound in deutro-chloroform were as shown below.

δ (ppm): 7.42 (1H, dd), 7.35 (1H, d), 4.51 (2H, s), 3.62 (3H, s), 2.75 (3H, s), 2.26 (3H, s), 1.37 (9H, s)

Compound 11: 2,3-Dimethyl-6-t-butyl-8-fluoro-4-acetoxy-acetylquinoline

In tetrahydrofuran (10 ml) was suspended 60% sodium hydride (44 mg). The compound 1 (200 mg) was added to the suspension under ice cooling, and the mixture was stirred for 30 min. Further, acetoxyacetyl chloride (100 μl) was added thereto, and the mixture was stirred for 3 hr. The reaction solution thus obtained was poured into ice water, and the mixture was extracted with ethyl acetate. The ethyl acetate layer was washed with a saturated aqueous sodium hydrogencarbonate solution and saturated brine and was then dried over anhydrous sodium sulfate. The solvent was then removed under the reduced pressure. The crude product was purified by chromatography on silica gel (Wako Gel C-200, elution solvent: n-hexane-ethyl acetate (3:1)) to give 2,3-dimethyl-6-t-butyl-8-fluoro-4-acetoxyacetylquinoline (compound 11, 140 mg). $^1$H-NMR data on this compound in deutro-chloroform were as shown below.

δ (ppm): 7.43 (1H, dd), 7.42 (1H, br.s), 5.02 (2H, s), 2.75 (3H, s), 2.27 (3H, s), 2.23 (3H, s), 1.40 (9H, s)

Compounds 12 to 14 (Comparative)

Compounds 12 to 14 having respective structures as shown in Table 1 below were produced in the same manner as used in the production of the above compounds. These compounds 12 to 14 are comparative compounds relative to the present invention.

Production of Rice Blast Controlling Agents

Production Example 1

Wettable Powder

Intimate mixing was carried out according to the following formulation, and the mixture was ground to produce wettable powder.

| | |
|---|---|
| Compound 2 | 25 wt % |
| Clay | 30 wt % |
| Diatomaceous earth | 35 wt % |
| Calcium lignin sulfonate | 3 wt % |
| Polyoxyethylene alkylaryl ether | 7 wt % |

Production Example 2

Dust

Intimate mixing was carried out according to the following formulation to produce dust.

| | |
|---|---|
| Compound 2 | 2 wt % |
| Clay | 60 wt % |
| Talc | 37 wt % |
| Calcium stearate | 1 wt % |

Production Example 3

Emulsifiable Concentrate

Intimate mixing and dissolution were carried out according to the following formulation to produce an emulsifiable concentrate.

| | |
|---|---|
| Compound 2 | 20 wt % |
| N,N-Dimethylformamide | 20 wt % |
| Xylene | 50 wt % |
| Polyoxyethylene alkylaryl ether | 10 wt % |

Evaluation Test

Test 1: Rice Blast Infection Inhibition Test (Rice Blast Preventive Test)

Full fourth-leaf stage rice seedlings (variety: Jikkoku) raised in each of plastic pots containing compost for about 15 days after seeding were provided as a test plant.

The rice blast controlling agent according to the present invention was diluted with a 10% aqueous acetone solution (with 2000-fold diluted Neoesterin® added thereto) to predetermined concentrations. Thus, test solution were prepared. Each of the test solution thus prepared was applied in an amount of 10 ml per three pots by means of a spray gun to the test plant, followed by air drying.

Next, rice blast fungi, which have been previously cultured in petri dish, were collected and were used to prepare a conidial suspension (1 to 5×10$^6$/ml). This conidial suspension was homogeneously sprayed and inoculated into the pots. The pots were then allowed to stand in a moist chamber of 25° C. for 24 hr. Thereafter, the pots were transferred to an environment controlled greenhouse kept at 20° C. at night and at 25° C. in the daytime to induce the disease.

Seven days after the inoculation, the number of lesions which had appeared in the fourth leaf were counted to obtain the results in the treated plot and the results in the nontreated plot. For each case, the protective value was calculated by the following equation.

Protective value=[1−(number of lesions in treated plot/number of lesions in nontreated plot)]×100

The results were as summarized in Table 1.

TABLE 1

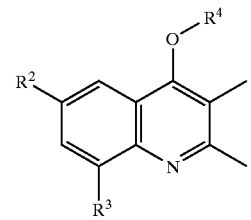

| Compound No. | R$^2$ | R$^3$ | R$^4$ | Concentration, ppm | Protective value |
|---|---|---|---|---|---|
| 1 | t-Bu | F | —H | 10 | 100 |
| | | | | 3 | 93 |
| 2 | t-Bu | F | —COCH$_3$ | 10 | 100 |
| | | | | 3 | 94 |
| 5 | t-Bu | F | —CO(CH$_2$)$_3$CH$_3$ | 10 | 99 |
| | | | | 3 | 84 |
| 6 | t-Bu | F | —COOCH$_3$ | 10 | 100 |
| | | | | 3 | 95 |
| 7 | t-Bu | F | —COOCH$_2$CH$_3$ | 10 | 100 |
| | | | | 3 | 95 |
| 8 | t-Bu | F | —COO(CH$_2$)$_2$CH$_3$ | 10 | 100 |
| | | | | 3 | 92 |
| 9 | t-Bu | F | —COO(CH$_2$)$_3$CH$_3$ | 10 | 99 |
| | | | | 3 | 90 |
| 10 | t-Bu | F | —COCH$_2$OCH$_3$ | 10 | 100 |
| | | | | 3 | 99 |

TABLE 1-continued

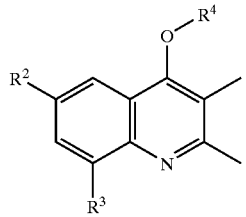

| Compound No. | R² | R³ | R⁴ | Concentration, ppm | Protective value |
|---|---|---|---|---|---|
| 11 | t-Bu | F | —COCH₂OCOCH₃ | 10 | 100 |
| | | | | 3 | 94 |
| 12 (Comparative) | H | H | —COCH₃ | 200 | <49 |
| 13 (Comparative) | H | F | —COCH₃ | 200 | <49 |
| 14 (Comparative) | t-Bu | H | —COCH₃ | 20 | 98 |
| | | | | 5 | 70 |
| | | | | 3 | <49 |

Test 2: Rice Blast Lesion Evolution Inhibition Test (Rice Blast Treatment Test)

Full fourth-leaf stage rice seedlings (variety: Jikkoku) raised in each of plastic pots containing compost for about 15 days after seeding were provided as a test plant.

Rice blast fungi, which have been previously cultured in petri dish, were collected and were used to prepare a conidial suspension (1 to 5×10⁶/ml). This conidial suspension was homogeneously sprayed and inoculated into the pots. The pots were then allowed to stand in a moist chamber of 25° C. for 24 hr. Thereafter, the pots were transferred to an environment controlled greenhouse kept at 20° C. at night and at 25° C. in the daytime to induce the disease.

After the elapse of 48 hr from the inoculation, the rice blast controlling agent according to the present invention was brought to predetermined concentrations to prepare test solution. Each of the test solution was applied in an amount of 10 ml per three pots by means of a spray gun to the test plant, followed by air drying. Subsequently, the pots were again transferred to the environment controlled greenhouse to induce the disease.

Seven days after the inoculation, the number of lesions which had appeared in the fourth leaf were counted to obtain the results in the treated plot and the results in the nontreated plot. For each case, the protective value was calculated in the same manner as used in the infection inhibition test.

The results were as shown in Table 2.

TABLE 2

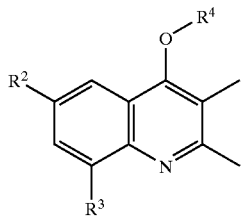

| Compound No. | R² | R³ | R⁴ | Concentration, ppm | Protective value |
|---|---|---|---|---|---|
| 2 | t-Bu | F | —COCH₃ | 75 | 98 |
| | | | | 37.5 | 90 |

TABLE 2-continued

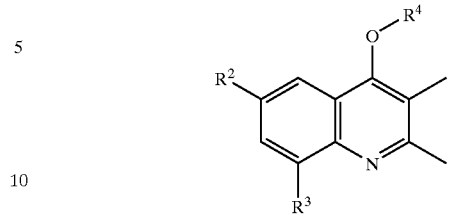

| Compound No. | R² | R³ | R⁴ | Concentration, ppm | Protective value |
|---|---|---|---|---|---|
| 3 | t-Bu | F | —COCH₂CH₃ | 75 | 89 |
| | | | | 37.5 | 64 |
| 4 | t-Bu | F | —CO(CH₂)₂CH₃ | 75 | 94 |
| | | | | 37.5 | 66 |
| 5 | t-Bu | F | —CO(CH₂)₃CH₃ | 75 | 95 |
| | | | | 37.5 | 82 |
| 6 | t-Bu | F | —COOCH₃ | 75 | 92 |
| | | | | 37.5 | 68 |
| 7 | t-Bu | F | —COOCH₂CH₃ | 100 | 98 |
| | | | | 30 | 87 |
| 8 | t-Bu | F | —COO(CH₂)₂CH₃ | 100 | 98 |
| | | | | 30 | 84 |
| 9 | t-Bu | F | —COO(CH₂)₃CH₃ | 100 | 98 |
| | | | | 30 | 87 |
| 10 | t-Bu | F | —COCH₂OCH₃ | 100 | 100 |
| | | | | 30 | 90 |
| 11 | t-Bu | F | —COCH₂OCOCH₃ | 100 | 99 |
| | | | | 30 | 88 |
| 12 (Comparative) | H | H | —COCH₃ | 100 | <49 |
| 13 (Comparative) | H | F | —COCH₃ | 100 | <49 |
| 14 (Comparative) | t-Bu | H | —COCH₃ | 100 | 81 |
| | | | | 50 | <49 |

What is claimed is:

1. A compound of formula (1) or an acid addition salt thereof:

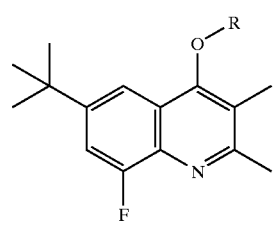

(1)

wherein

R represents a hydrogen atom, —COR¹, —COOR¹, in which R¹ represents alkyl having 1 to 4 carbon atoms, —COCH₂OCH₃, or —COCH₂OCOCH₃.

2. A composition for controlling rice blast, comprising at least one compound selected from the group consisting of the compounds of formula (1) according to claim 1 or acid addition salts thereof, and a carrier.

3. A method for controlling rice blast, comprising the step of applying an effective amount of the compound or acid addition salt thereof according to claim 1 to a rice plant per se, soil, or field water.

4. The compound of formula (1) according to claim 1 or an acid addition salt thereof, wherein the compound is 2,3-dimethyl-6-t-butyl-8-fluoro-4-hydroxyquinoline.

5. The compound of formula (1) according to claim 1 or an acid addition salt thereof, wherein the compound is 2,3-dimethyl-6-t-butyl-8-fluoro-4-acetylquinoline.

6. The compound of formula (1) according to claim 1 or an acid addition salt thereof, wherein the compound is 2,3-dimethyl-6-t-butyl-8-fluoro-4-propionyl-quinoline.

7. The compound of formula (1) according to claim 1 or an acid addition salt thereof, wherein the compound is 2,3-dimethyl-6-t-butyl-8-fluoro-4-butrylquinoline.

8. The compound of formula (1) according to claim 1 or an acid addition salt thereof, wherein the compound is 2,3-dimethyl-6-t-butyl-8-fluoro-4-valerylquinoline.

9. The compound of formula (1) according to claim 1 or an acid addition salt thereof, wherein the compound is 2,3-dimethyl-6-t-butyl-8-fluoro-4-methozycarbonylquinoline.

10. The compound of formula (1) according to claim 1 or an acid addition salt thereof, wherein the compound is 2,3-dimethyl-6-t-butyl-8-fluoro-4-ethoxycarbonylquinoline.

11. The compound of formula (1) according to claim 1 or an acid addition salt thereof, wherein the compound is 2,3-dimethyl-6-t-butyl-8-fluoro-4-n-propoxycarbonylquinoline.

12. The compound of formula (1) according to claim 1 or an acid addition salt thereof, wherein the compound is 2,3-dimethyl-6-t-butyl-8-fluoro-4-n-butoxycarbonylquinoline.

13. The compound of formula (1) according to claim 1 or an acid addition salt thereof, wherein the compound is 2,3-dimethyl-6-t-butyl-8-fluoro-4-methoxyacetylquinoline.

14. The compound of formula (1) according to claim 1 or an acid addition salt thereof, wherein the compound is 2,3-dimethyl-6-t-butyl-8-fluoro-4-acetoxyacetylquinoline.

* * * * *